Figure 1:
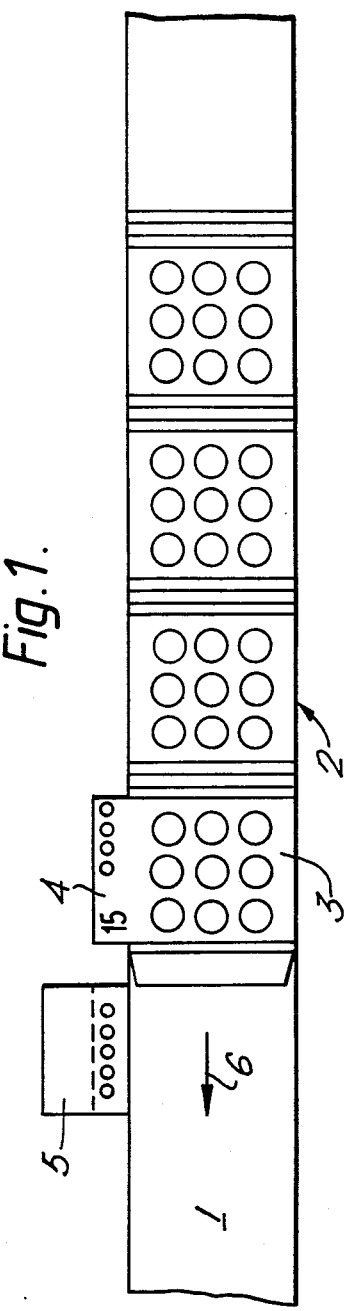

United States Patent [19]

Suovaniemi et al.

[11] 4,431,924

[45] Feb. 14, 1984

[54] CODE SYSTEM IN A MULTI-CHANNEL ANALYSIS EQUIPMENT AND A DEVICE RELATED TO THE SYSTEM

[75] Inventors: Osmo Suovaniemi, Helsinki; Esko Kaukanen, Espoo; Pertti Ekholm, Helsinki, all of Finland

[73] Assignee: Labsystems Oy, Helsinki, Finland

[21] Appl. No.: 252,173

[22] Filed: Apr. 8, 1981

[30] Foreign Application Priority Data

Apr. 28, 1980 [FI] Finland ................................ 801356

[51] Int. Cl.³ .............................................. G06K 7/10
[52] U.S. Cl. ..................................... 250/566; 356/244
[58] Field of Search ................ 356/71, 244, 246, 440; 250/566, 568, 576, 328; 235/456, 460, 470, 494

[56] References Cited

U.S. PATENT DOCUMENTS 3,656,833  4/1972  Wallace .............................. 356/244
4,004,150  1/1977  Natelson ............................. 250/576
4,118,280  10/1978 Charles et al. ..................... 356/244

*Primary Examiner*—David C. Nelms
*Attorney, Agent, or Firm*—Hopgood, Calimafde, Kalil, Blaustein & Judlowe

[57] ABSTRACT

A code system for the identification of a sample group to be measured in a multi-channel photometer or in any other multi-channel analysis equipment, e.g. in a spectrophotometer, fluorometer, luminometer, turbidometer, nefelometer, cell counter, or isotope counter. The samples to be measured have been fitted in the matrix form into cuvette sets, sets of test tubes, or pit plates, and the measurement takes place preferably in the vertical direction. The sample group to be measured is provided with a related code piece, such as a code plate, containing the measurement points to be ready by means of the analysis equipment. According to the invention, the measurement points of the code piece are in the same order and with the same relative distances as compared with the measurement channels of the said multi-channel photometer or any other multi-channel analysis equipment, or with a part of or a multiple of said channels. The code piece is arranged so as to be readable by means of the measurement channels of the multi-channel photometer or any other multi-channel analysis equipment in one or several subsequent steps without using a separate code reader.

3 Claims, 5 Drawing Figures

CODE SYSTEM IN A MULTI-CHANNEL ANALYSIS EQUIPMENT AND A DEVICE RELATED TO THE SYSTEM

The subject of the present invention is a code system for the identification of a sample group to be measured in a multi-channel photometer or in any other multi-channel analysis equipment, e.g. in a spectrophotometer, fluorometer, luminometer, turbidometer, nefelometer, cell counter, or isotope counter, the samples to be measured having been fitted in the matrix form into cuvette sets, sets of test tubes, or pit plates and the measurement preferably taking place in the vertical direction, and the sample group to be measured being provided with a related code piece, such as a code plate, containing the measurement points to be read by means of the analysis equipment.

When a different analysis is being performed, a major problem is the identification of the samples and of the reaction mixtures present at different stages. The development of methods and equipment of identification of samples was little in the 1970's. Highly usable methods of identification of samples have become the BAR code and the OCR (optical character recognition). In analyzer systems of different types, these codes are read by means of separate code reader devices. It is to be considered a remarkable drawback that two separate reading systems are required: the measurement equipment proper for the analysis equipment and a separate code reading system.

The object of the present invention is to eliminate the above drawback, and the code system in accordance with the invention is mainly characterized in that the measurement points of the code piece are in the same order and with the same relative distances as compared with the measurement channels of the said multi-channel photometer or any other multi-channel analysis equipment, or with a part of or a multiple of said channels, the code piece being arranged so as to be readable by means of the measurement channels of the multi-channel photometer or any other multi-channel analysis equipment in one or several subsequent steps without using a separate code reader.

The invention also comprises a device for the code system in accordance with the invention, and the features characteristic of the said device come out from claim 3.

Figure 3:
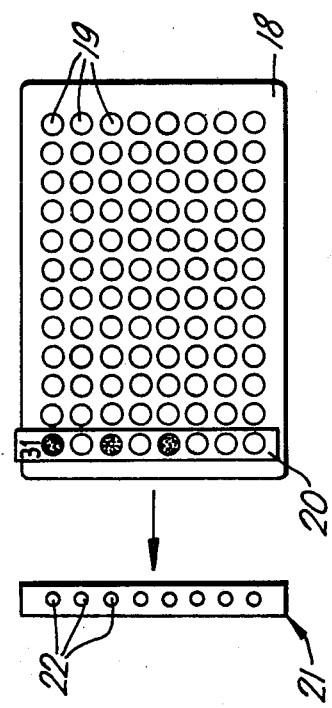
Figure 2:
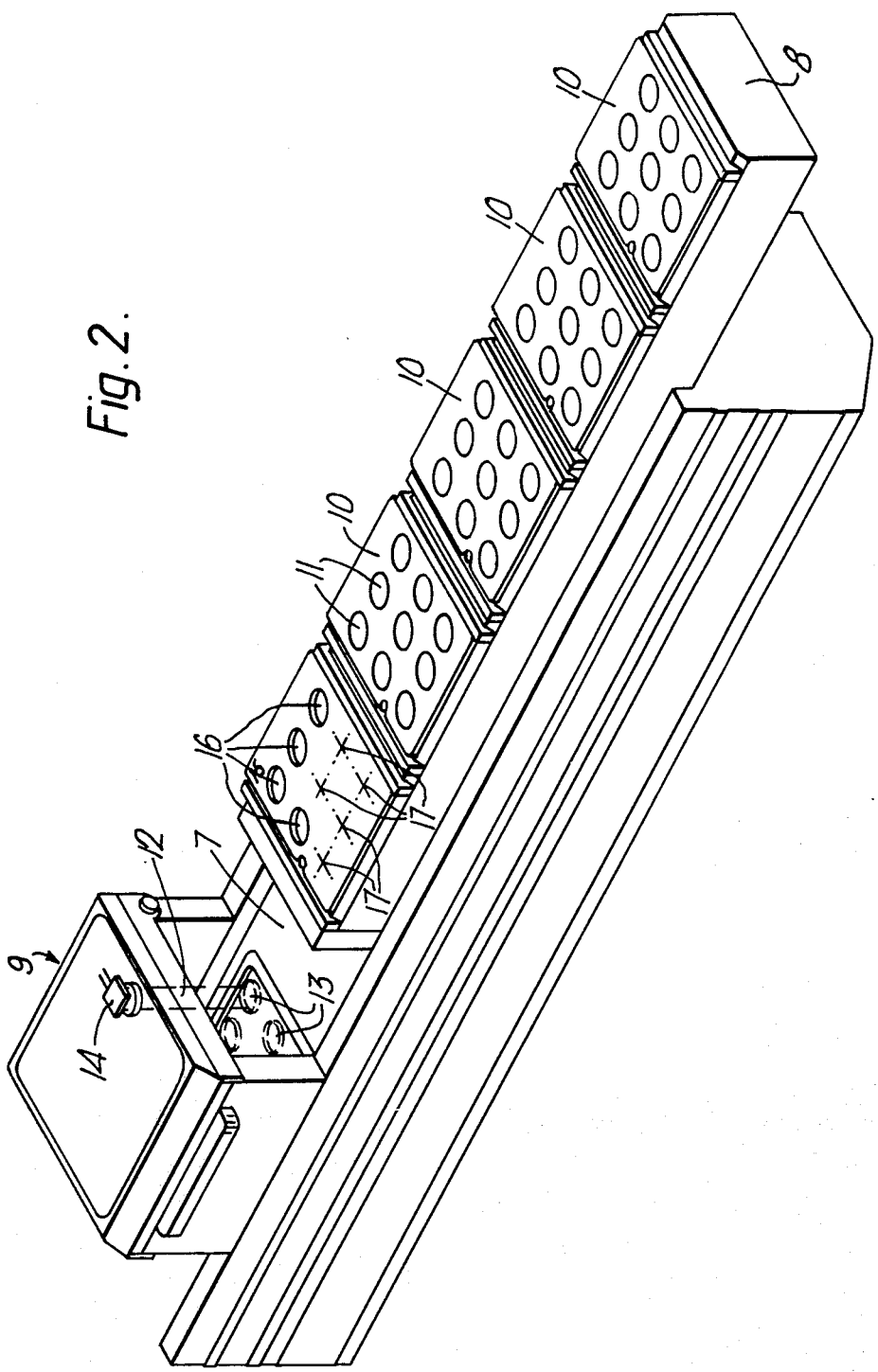
Figure 4:
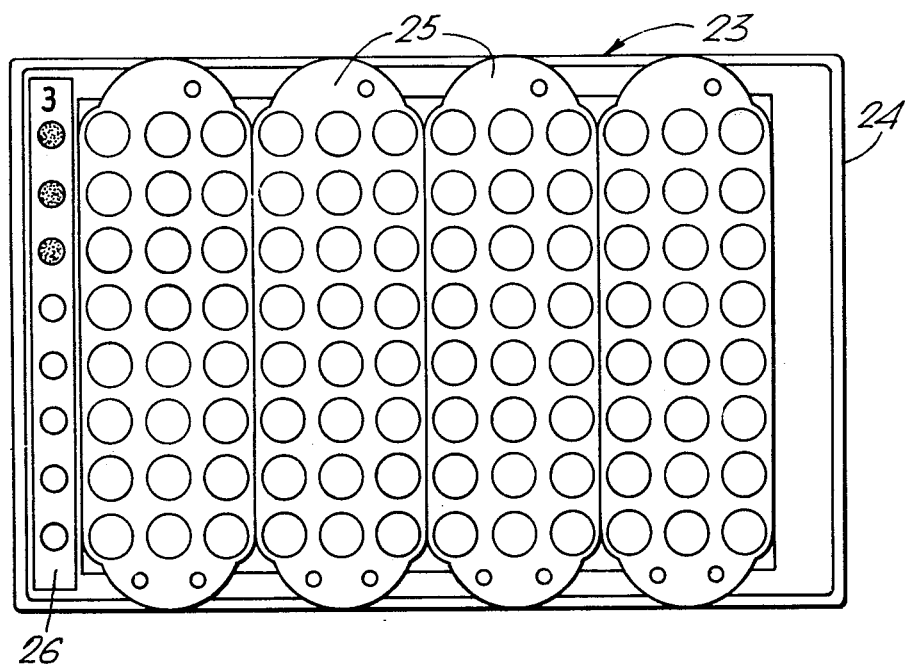
Figure 5:
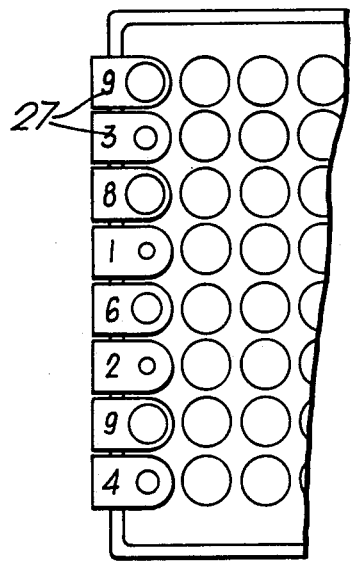

The invention comes out more closely from the following description and from the attached drawings, wherein FIG. 1 is a schematical top view of a conventional arrangement for the identification of cuvette sets, whereby a code attached to the cuvette set is read by means of a separate code reader, FIG. 2 is an axonometric presentation of a photometric arrangement provided with a code system in accordance with the present invention, together with the cuvette groups, FIG. 3 shows a so-called microtiter disk as viewed from the top and as provided with a code tape placed above one line, FIG. 4 shows a set of microcuvettes consisting of a frame part and of cuvette set components attached to same, as provided with a code and as viewed from above, and FIG. 5 shows an end of a microtiter disk in accordance with FIG. 3 as viewed from above and with the first line being provided with code particles.

In FIG. 1, a measurement cassette 2 is fitted on the measurement path 1 of the photometer, to which cassette the cuvette set 3 to be measured, provided with a code strip 4, is fitted. Alongside the measurement path 1, facing the code strip 4, there is a code reader 5, which is fitted so as to read the code in the code strip 4 when the measurement cassette 2 proceeds in the direction of the arrow 6. In such a system the photometer comprises the measurement head proper, including the sources of light and the receivers, the working-up part so as to obtain the value of optical density from the measurement signal, the data processing part (microprocessor, computer or equivalent), as well as the output part, whereby to the data processing part, corresponding the measurement side proper, there is a connection from the code reader, including the necessary sources of light, receivers, etc., as well as from the subsequent working-up part in order to transfer the information obtained from the code reader to the data processing part.

The essential idea of the present invention lies therein that for reading the code no separate code reader is used at all, but the multi-channel measurement head itself is used for reading the code, and the code is arranged into the form required by the said procedure.

The arrangement in accordance with the invention comes out from FIG. 2, wherein a measurement cassette 8 has been fitted onto the measurement path 7 of the photometer, the samples placed in the cuvette sets 10 and to be measured in the measurement head 9 of the photometer having been fitted onto the said cassette 8. In the case shown in FIG. 2 each cuvette set 10 includes nine cuvettes 11, which are arranged in a 3×3 matrix form. Correspondingly, the measurement head 9 of the photometer has nine channels, so that it can simultaneously measure the nine cuvettes 11 of one cuvette set 10. In the measurement head 9 the measurement beams 12 pass vertically from the sources of light 13 to the corresponding detectors 14. Thus, there are 9 pairs of light-source-detector in the measurement head 9 of the photometer, and, in the present case, they are of course also positioned in the 3×3 matrix form. In addition to the cuvette sets 10, the beginning of the measurement cassette 8 is provided with a code piece 15, which consists of a code plate including the photometrically readable measurement points 16 and 17. These measurement points 16 and 17 are arranged in the same order and with the same relative distances as compared with the measurement channels in the measurement head 9 of the multi-channel photometer, or with a part of or a multiple of the said measurement channels. The measurement points in the piece shown in FIG. 2 consist of holes 16 made into the code plate 15 and placed at the specified measurement locations and of a non-transparent disk placed at the specified measurement locations 17, or of holes covered in a corresponding way. In such a case the code piece 15 can be read in the measurement head 9 of the multi-channel photometer by means of the measurement channels without using a separate code reader.

FIG. 3 shows a so-called microtiter disk 18 and therein locations 19 for samples or reaction mixture. In this embodiment the code piece consists of one line in the microtiter disk 18, which line is covered by a code tape 20. The code for the line concerned is formed so that the code tape 20 covers a part of the sample or reaction mixture locations 19 in the line concerned but leaves some of the locations fully open. The microtiter disk 18 with its code is read in the measurement head 21 of the measurement device, wherein pairs of light-source-detector 22 correspond the sample or reaction mixture locations 19 of each line.

FIG. 4 shows a microcuvette set 23 in accordance with the Finnish Patent Application No. 790692, which set consists of a frame part 24 and of cuvette set components 25 supported by the frame part, whereby the frame part 24 is coded in accordance with the present invention. For the code, the front or rear edge of the frame part 24 is provided with a line of holes 26, wherein some of the holes are covered, e.g., with a non-transparent tape. Such a code line placed in the frame part 24 can be read in the measurement head of the photometer in the same way as was described above. Above, embodiments have been described in which all the code pieces have such measurement points of which some are covered by a code tape, as desired. When a photometer is used for reading the code, the measurement point may, of course, also be of some other type except a fully transparent measurement point, for example a hole or a non-transparent measurement point, e.g. a covered hole. The measurement points may also be partly transparent data elements in the code. Of course, it is also possible to use, as data elements of the measurement points, code solutions having different absorbance numbers or, e.g., extruded code particles 27, which are penetrable to measurement light to different extents (FIG. 5). Most appropriately, the code is also visually readable. The same of course also applies to other types of multi-channel analysis equipment, such as, e.g., spectrophotometers, cell counters, and isotope counters when the procedure is such that the measurement points of the code piece can be measured by means of the measurement beams, counters or detectors of the analysis equipment concerned.

What is claimed is:

1. A coding system for multiple channel optical analysis equipment comprising:
   a sample holder including a plurality of specimen wells into which the specimens to be analyzed are disposed, said specimens wells being arranged in a matrix; and
   a code piece mounted on said sample holder for indicating the measurement points to be read by said optical analysis equipment, said code piece including optical indicia means for reading by said optical analysis equipment, said indicia means being arranged in the same order and with the same relative distances as at least one row of said matrix of said specimen wells and said measurement channels of said optical analysis equipment.

2. The coding system as claimed in claim 1 wherein said indicia means comprise light attenuating means having varying degrees of light attenuation for reading by said optical analysis equipment.

3. The coding system as claimed in claim 1 wherein said indicia means of said code piece are arranged in the same order and with the same relative distance of at least one row and two columns of said matrix of specimen wells.

* * * * *